US012765890B2

(12) United States Patent
Firmbach et al.

(10) Patent No.: US 12,765,890 B2
(45) Date of Patent: Oct. 20, 2026

(54) SURGICAL DEVICE

(71) Applicant: Aesculap AG, Tuttlingen (DE)

(72) Inventors: Franz-Peter Firmbach, Emmingen-Liptingen (DE); Lilli Stoffels, Calw (FR)

(73) Assignee: Aesculap AG, Tuttlingen (DE)

( * ) Notice: Subject to any disclaimer, the term of this patent is extended or adjusted under 35 U.S.C. 154(b) by 483 days.

(21) Appl. No.: 18/334,973

(22) Filed: Jun. 14, 2023

(65) Prior Publication Data

US 2023/0404604 A1 Dec. 21, 2023

(30) Foreign Application Priority Data

Jun. 20, 2022 (DE) .................... 10 2022 206 117.9

(51) Int. Cl.
*A61B 17/17* (2006.01)
*A61B 17/15* (2006.01)

(52) U.S. Cl.
CPC ........ *A61B 17/1764* (2013.01); *A61B 17/157* (2013.01)

(58) Field of Classification Search
CPC . A61F 2002/4668; A61F 2/4657; A61B 17/64
USPC .......................................................... 606/102
See application file for complete search history.

(56) References Cited

U.S. PATENT DOCUMENTS 5,162,039 A * 11/1992 Dahners .................... A61F 5/04 602/23
5,197,944 A * 3/1993 Steele .................. A61B 17/157 606/86 R
5,514,143 A 5/1996 Bonutti et al.
5,611,353 A * 3/1997 Dance .................... A61B 34/20 600/595
6,024,746 A * 2/2000 Katz .................. A61B 17/1767 606/88
6,258,096 B1 * 7/2001 Seki ..................... A61B 17/155 606/88

(Continued)

FOREIGN PATENT DOCUMENTS

DE 102020110346 A1 10/2021
GB 2398011 A 11/2004

(Continued)

*Primary Examiner* — David W Bates
(74) *Attorney, Agent, or Firm* — Christopher A. Rothe; CM Law

(57) ABSTRACT

A surgical device and surgical system for use in a total knee arthroplasty. The surgical device is configured for aligning an extramedullary alignment rod, and has a supporting portion having at least two supporting geometries. The supporting geometries are each adapted for support on an anterior edge of a tibia. A reference portion projects in an anterior direction from the supporting portion and has at least two reference geometries that are separated from one another along a reference line that extends in a proximodistal direction. The reference line is separated from the supporting line by an anterior distance and extends parallel to the supporting line. The reference geometries and/or the reference line serve as a reference for aligning the extramedullary alignment rod instead of the anterior edge of the tibia. The reference geometries are each adapted for at least mediolaterally form-fit mounting of the extramedullary alignment rod.

14 Claims, 9 Drawing Sheets

(56) References Cited

U.S. PATENT DOCUMENTS

| | | | | |
|---|---|---|---|---|
| 6,327,491 | B1 * | 12/2001 | Franklin | A61B 34/20<br>600/429 |
| 7,488,324 | B1 * | 2/2009 | Metzger | A61F 2/4657<br>600/587 |
| 2004/0015173 | A1 * | 1/2004 | Irving | A61B 17/157<br>606/88 |
| 2006/0149288 | A1 * | 7/2006 | Florentino | A61F 2/4657<br>606/102 |
| 2008/0132818 | A1 * | 6/2008 | Livorsi | A61B 17/154<br>602/23 |
| 2010/0234850 | A1 * | 9/2010 | Dees, Jr. | A61B 17/157<br>29/428 |
| 2012/0101504 | A1 * | 4/2012 | Habegger | A61B 17/157<br>606/88 |
| 2021/0000484 | A1 * | 1/2021 | Goble | A61B 17/164 |
| 2021/0282791 | A1 | 9/2021 | Oh | |
| 2023/0063563 | A1 * | 3/2023 | Firmbach | A61B 17/157 |

FOREIGN PATENT DOCUMENTS

| | | | | |
|---|---|---|---|---|
| WO | 2020013584 | A1 | 1/2020 | |
| WO | WO-2005110249 | A1 * | 11/2025 | A61B 17/158 |

* cited by examiner

SURGICAL DEVICE

CROSS-REFERENCE TO RELATED APPLICATION(S)

This application claims priority under 35 U.S.C. § 119 to German Application No. 2022 206 117.9, filed on Jun. 20, 2022, the content of which is incorporated by reference herein in its entirety.

FIELD

The present disclosure relates to a surgical device for aligning an extramedullary alignment rod during a total knee arthroplasty.

BACKGROUND

In a total knee arthroplasty (TKA), articular surfaces of the femur and/or tibia that are worn or affected by disease or an accident are replaced with artificial articular surfaces of a knee joint prosthesis. Such knee joint prostheses conventionally comprise a femoral component and a tibial component. The femoral component is implanted at the distal end of the femur. The tibial component is implanted at the proximal end of the tibia.

Before the implantation of the prosthetic components, the distal femur and the proximal tibia are resected. For this purpose, the surgeon makes various resection cuts and separates bone material and/or cartilage material from the bone in question. By the resection, the bone is matched in its shape to the prosthetic component to be received.

The resection may be carried out on the basis of various concepts. One concept aims to keep the tensions of the ligaments of the knee balanced during the articular movement. In this way, a better function of the knee joint prosthesis is intended to be achieved. This concept is generally referred to as "gap balancing". In other concepts, the surgeon removes a certain amount of bone material and/or cartilage material by means of the resection. Such concepts are generally referred to as "measured resection". The alignment of the resection cuts in relation to the anatomy of the patient determines the future alignment of the implanted components and consequently also the orientation of the prosthetic articular axes. The alignment of the resection cuts is therefore of particular importance.

For the alignment of the resection cuts, distinction can be made between three approaches: mechanical, anatomical and kinematic. In the case of mechanical alignment, the proximal tibia is resected perpendicularly to the longitudinal axis of the tibial shaft. The resection of the distal femur is carried out in a way which is matched thereto. If necessary, ligament releases are carried out. In the case of anatomical alignment, an attempt is made to resect the tibia at a *varus* angle of 3°. The femoral resection and ligament releases are carried out with the aim of a straight hip-knee-ankle axis of the leg. The aim of kinematic alignment (abbreviated below to KA) is to implant the artificial articular surfaces of the prosthetic components at the level of the pre-arthritic, defect-free natural articular surfaces.

During a KA, alignment of the resection cuts is often carried out starting from the distal femur. The resection of the proximal tibia is carried out in a way which is matched thereto. In this context, the term transfer of the alignments and/or cuts onto the tibia is also used. For this purpose, special surgical instruments are known, which are also referred to as a tibial alignment and/or transfer tool (tibial cut alignment guide). Such instruments make it possible to transfer the alignment of the femoral resection cuts onto the tibia, and they often have an extramedullary alignment rod. In a conventional procedure, a parallel alignment of the extramedullary alignment rod with respect to the anterior edge of the tibia is sought.

SUMMARY

It is an object of the present disclosure to allow simplified and particularly precise parallel alignment of the extramedullary alignment rod.

The surgical device according to the present disclosure has: a supporting portion having at least two supporting geometries, which are separated from one another along a supporting line that extends in a proximodistal direction and are each adapted for support on an anterior edge of a tibia, and a reference portion, which projects in an anterior direction from the supporting portion and has at least two reference geometries, which are separated from one another along a reference line that extends in a proximodistal direction, wherein the reference line is separated from the supporting line by an anterior distance and extends parallel to the supporting line, wherein the at least two reference geometries and/or the reference line serve as a reference for aligning the extramedullary alignment rod instead of the anterior edge of the tibia, and wherein the at least two reference geometries are each adapted for at least mediolateral form-fit mounting of the extramedullary alignment rod. The device according to the present disclosure allows particularly precise and simplified parallel alignment of the extramedullary alignment rod. The supporting line that extends in a proximodistal direction between the at least two supporting geometries bears on the anterior edge of the tibia during use. This will also be referred to below as the tibial front edge. In various embodiments, the at least two supporting geometries are configured differently and may for example be "pointwise", linear or two-dimensional. The at least two supporting geometries of the supporting portion are separated from one another along the tibial front edge during use of the surgical device. The supporting portion may in principle have any desired shape. The same applies correspondingly for the reference portion. The at least two reference geometries of the reference portion are separated from one another along the tibial front edge during use of the surgical device. The reference line extends between the at least two reference geometries and is offset in the anterior direction parallel to the supporting lines—and therefore also the tibial front edge. In relation to a supine position of the patient, the reference line is consequently arranged above the tibial front edge by the (anterior) distance. The reference line and/or the reference geometries are used for the actual parallel alignment of the extramedullary alignment rod. Because of the anterior separation of the reference line and/or of the reference geometries, the extramedullary alignment rod lies closer in the anteroposterior direction to the reference line and/or the reference geometries than to the tibial front edge. Owing to the distance, which is to this extent reduced, the surgeon can establish more easily and more precisely whether or not a parallel alignment exists. This is particularly true when the patient has a pronounced *varus-valgus* angulation of the tibia. Setting up the at least two reference geometries for the form-fit mounting of the extramedullary alignment rod also contributes to particularly easy and precise parallel alignment of the extramedullary alignment rod. This is because the form-fit mounting on the at least two reference geometries counteracts an undesired relative displacement of the extramedullary alignment rod. In this way, an erroneous in alignment is avoided. The form-fit mounting acts at least in a mediolateral direction. In addition, a form fit may be provided in the anteroposterior direction. Preferably, the at least two reference geometries are each adapted for mounting of the extramedullary alignment rod in proximodistal gliding movement. In various embodiments, the at least two reference geometries are configured differently, for example respectively as an indentation, notch, recess, furrow, groove and/or bore. The said form fit is releasable, and may for example be configured in the form of a latch, plug, clamp and/or snap connection. In one embodiment, the surgical device is configured in one piece. In another embodiment, the surgical device is constructed in multiple pieces. In one embodiment, the reference portion and the supporting portion are manufactured continuously in one piece. In another embodiment, the said portions are manufactured as separate component parts and are joined together. The surgical device is preferably manufactured from a plastic material and/or metal. In one embodiment, the surgical device is a disposable device for single use. In another embodiment, the surgical device is a reusable device for multiple use. The extramedullary alignment rod is not a constituent part of the surgical device.

The positional and directional terminology used in this description refer to the body of a patient, in particular the patient's tibia, and to this extent are to be understood according to their conventional anatomical meaning. Consequently, "anterior" means front or lying at the front, "posterior" means rear or lying at the rear, "medial" means inner or lying inwards, "lateral" means outer or lying outwards, "proximal" means towards the centre of the body and "distal" means away from the centre of the body. Furthermore, "proximodistal" means along, preferably parallel to an axis aligned in a proximal-distal direction, "anteroposterior" means along, preferably parallel to an axis aligned in an anterior-posterior direction and "mediolateral" means along, preferably parallel to an axis aligned in a medial-lateral direction. Said axes are aligned orthogonally to one another and may, of course, be set in relation to X, Y and Z axes that are not connected with the anatomy of the patient. For example, the proximal-distal axis may alternatively be referred to as the X axis. The medial-lateral axis may be referred to as the Y axis. The anterior-posterior axis may be referred to as the Z axis. For improved illustration and for the sake of simplicity, said anatomical positional and directional terminology will primarily be used below. Furthermore, terms such as "upper side" will be used in relation to a posteriorly directed viewing direction. Terms such as "lower side" will be used in relation to an anteriorly directed viewing direction.

In one embodiment of the present disclosure, the reference portion has at least two first reference geometries, which are separated from one another along a first reference line, and two second reference geometries, which are separated from one another along a second reference line, the first reference line being separated by an anterior first distance from the supporting line and the second reference line being separated by an anterior second distance from the supporting line. By virtue of the different distances of the at least two reference lines and/or respectively associated reference geometries, the surgical device can be used on different sizes of bone structures. Expressed in other words, the surgical device may readily be used for patients of different size. It is to be understood that both the first reference line and the second reference line extend in a proximodistal direction and parallel to the supporting lines. In relation to a supine position of the patient, the reference lines are arranged above one another. Preferably, the surgical device has a multiplicity of pairwise arranged reference geometries, each having an associated reference line. Preferably, there are more than five, preferably more than ten, particularly preferably more than twenty reference lines. In this way, the extramedullary alignment rod can be aligned in a particularly precise and finely graduated way at different distances parallel to the tibial front edge.

In another embodiment of the present disclosure, the reference geometries are each configured as a bore, so that there are at least two first bores and two second bores. By such a configuration of the reference geometries, the extramedullary alignment rod can be mounted particularly simply and reliably with a form fit. It also leads to simple and economical manufacture of the reference geometries and therefore also of the surgical device. The bores are each elongated along a proximodistal direction and along their associated reference line. The two first bores and the two second bores respectively form a bore pair. During use, the extramedullary alignment rod is releasably mounted with a form fit on and/or in a pair of the bores, for example on and/or in the two first bores or the two second bores. The mounting is at least mediolaterally form-fit. In addition, there may be a form fit, in particular a releasable form fit, in the anteroposterior direction. Preferably, the extramedullary alignment rod is movable by gliding in the longitudinal direction of the bores. Preferably, an outer diameter of the extramedullary alignment rod and an inner diameter of the bores are tailored to one another in such a way that mounting without play is achieved. Preferably, the bores each have a round, preferably circular cross section.

In another embodiment of the present disclosure, the first bores and the second bores are connected to one another in an anteroposterior direction, so that the extramedullary alignment rod can be displaced starting from a mounting position on the two first bores in an anteroposterior direction and/or in its radial direction into a mounting position on the two second bores, and vice versa. In this way, the extramedullary alignment rod can be displaced between different anterior distances/positions, without it having for this purpose to be extracted axially from the first bores and then inserted into the second bores, or vice versa. The anteroposterior connection between the bores may, for example, be configured in the form of a slot. Alternatively or additionally, bores may form a row of bores or holes, a distance between neighbouring bore midpoints being less than a diameter of the bores. In one embodiment, the bores are each resiliently flexible in the radial direction. This simplifies relocation of the extramedullary alignment rod between neighbouring bores and/or different anterior distances and/or from one of the bore pairs into another of the bore pairs. In another embodiment, the extramedullary alignment rod alternatively or additionally has a rotationally asymmetrical cross section. For relocation between neighbouring bores, the extramedullary alignment rod can be rotated about its longitudinal axis so that it can be guided through the respective connection between the neighbouring bores.

In another embodiment of the present disclosure, the reference portion is resiliently flexible in the region of the bores. By virtue of the resilient flexibility, the extramedullary alignment rod can be moved particularly easily in the anteroposterior direction from one of the bore pairs into another of the bore pairs. The resilient flexibility is in one embodiment due to the material. For example, the reference portion may be manufactured from a flexible plastic at least in the region of the bores. In another embodiment, the resilient flexibility is alternatively or additionally due to the configuration. For example, the reference portion may be configured with thin walls at least in the region of the bores.

In another embodiment of the present disclosure, the reference portion is configured as a frame having two longitudinal branches and one transverse branch, the two longitudinal branches being separated from one another in a proximodistal direction and each being elongated in an anteroposterior direction and having the reference geometries, and the transverse branch being elongated in a proximodistal direction between the two longitudinal branches and connecting the latter to one another. This is a particularly preferred embodiment of the present disclosure. If the reference geometries are each configured as a bore, they each extend in a proximodistal direction through one of the longitudinal branches. Preferably, the transverse branch is arranged at one end of the two longitudinal branches and the supporting portion is arranged and/or formed at the other end of the longitudinal branch. Preferably, the longitudinal branches are elongated parallel to one another. Preferably, the transverse branch is elongated parallel to the supporting line and/or the reference line/lines. The transverse branch is used on the one hand as a connecting element between the two longitudinal branches. Alternatively or additionally, the transverse branch is used as a handle for easy handling of the surgical device. In an alternative embodiment, there are only the two longitudinal branches, but not the transverse branch.

In another embodiment of the present disclosure, the longitudinal branches each have a row of bores with a multiplicity of bores following one another in an anteroposterior direction as reference geometries. This is a particularly preferred embodiment of the present disclosure. The bores of the rows of bores are preferably connected to one another in an anteroposterior direction. Expressed in other words, the bores of a row of bores merge into one another, preferably in a radial direction.

In another embodiment of the present disclosure, the supporting portion is formed by end portions of the longitudinal branches, each end portion respectively having one of the supporting geometries. In this embodiment, the end portions of the longitudinal branches together form feet or foot portions for support on the tibial front edge. In this way, a particularly simple construction of the surgical device is achieved. The longitudinal branches are each elongated between a first end and a second end. The supporting portion is, for example, formed by the two first ends. The transverse branch, if present, is in this case preferably elongated between the two second ends.

In another embodiment of the present disclosure, the supporting geometries each have a fork shape with a first prong portion and a second prong portion. Expressed in other words, the end portions of the longitudinal branches are each configured in the manner of a crutch having a first prong portion and a second prong portion. The fork shape counteracts slipping of the surgical device from the tibial front edge.

In another embodiment of the present disclosure, the supporting portion is configured as a plate having a lower side oriented in a posterior direction and an upper side oriented in an anterior direction, the lower side being plane and having and/or forming the at least two supporting geometries, and the reference portion projecting from the upper side. During use, the plate is set with its lower side foremost onto the tibial front edge. In one embodiment, the lower side has the at least two supporting geometries. These may for example each project in the shape of a fork in a posterior direction from the lower side according to the preceding embodiment. In another embodiment, the lower side itself forms the at least two supporting geometries. In this case, two "points", lines or surface portions of the lower side, which are separated from one another in a proximodistal direction, define the supporting geometries. The plate may have any desired base shape, a round, rectangular or triangular base shape being preferred.

In another embodiment of the present disclosure, the plate has a scale arranged on the upper side with graduations fanning out in a distal direction, the graduations each representing a value of a *varus/valgus* angle of the tibia. The scale allows easy reading and/or adjustment of the *varus/valgus* angle. By arranging the scale on the upper side, the surgeon can read the scale particularly easily and reliably.

The present disclosure furthermore relates to an arrangement having a surgical device according to the preceding description and having an extramedullary alignment rod. With regard to the features and advantages of the surgical device, reference is made to the preceding description. The extramedullary alignment rod is elongated between a first end and a second end. Preferably, one of the two ends is adapted for fastening on a tibial alignment and/or transfer tool.

BRIEF DESCRIPTION OF THE DRAWING FIGURES

Further advantages and features of the present disclosure may be found in the following description of preferred exemplary embodiments of the present disclosure, which are represented with the aid of the drawings.

DETAILED DESCRIPTION

Figure 1:
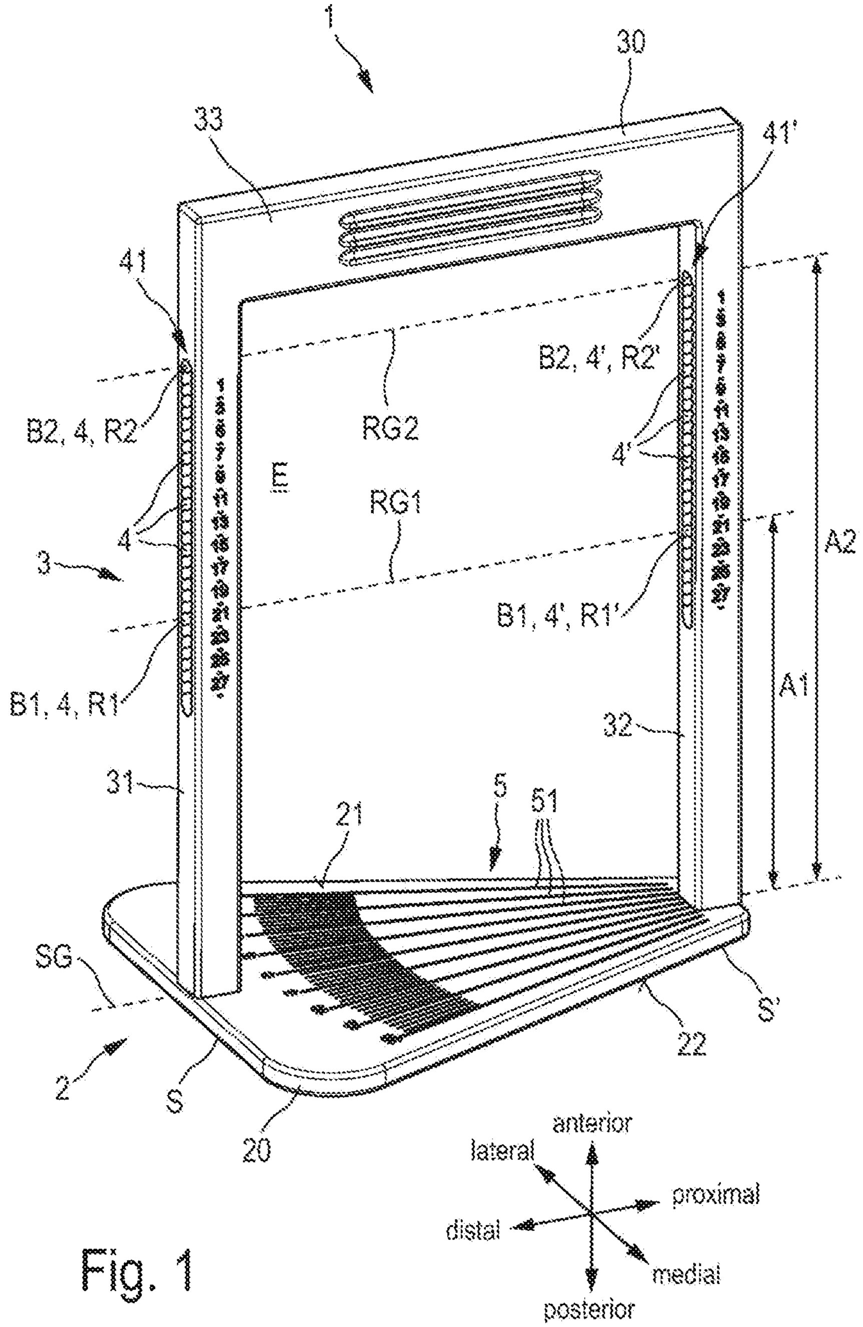
FIG. 1 shows a schematic perspective view of one embodiment of a surgical device according to the present disclosure.
Figure 2:
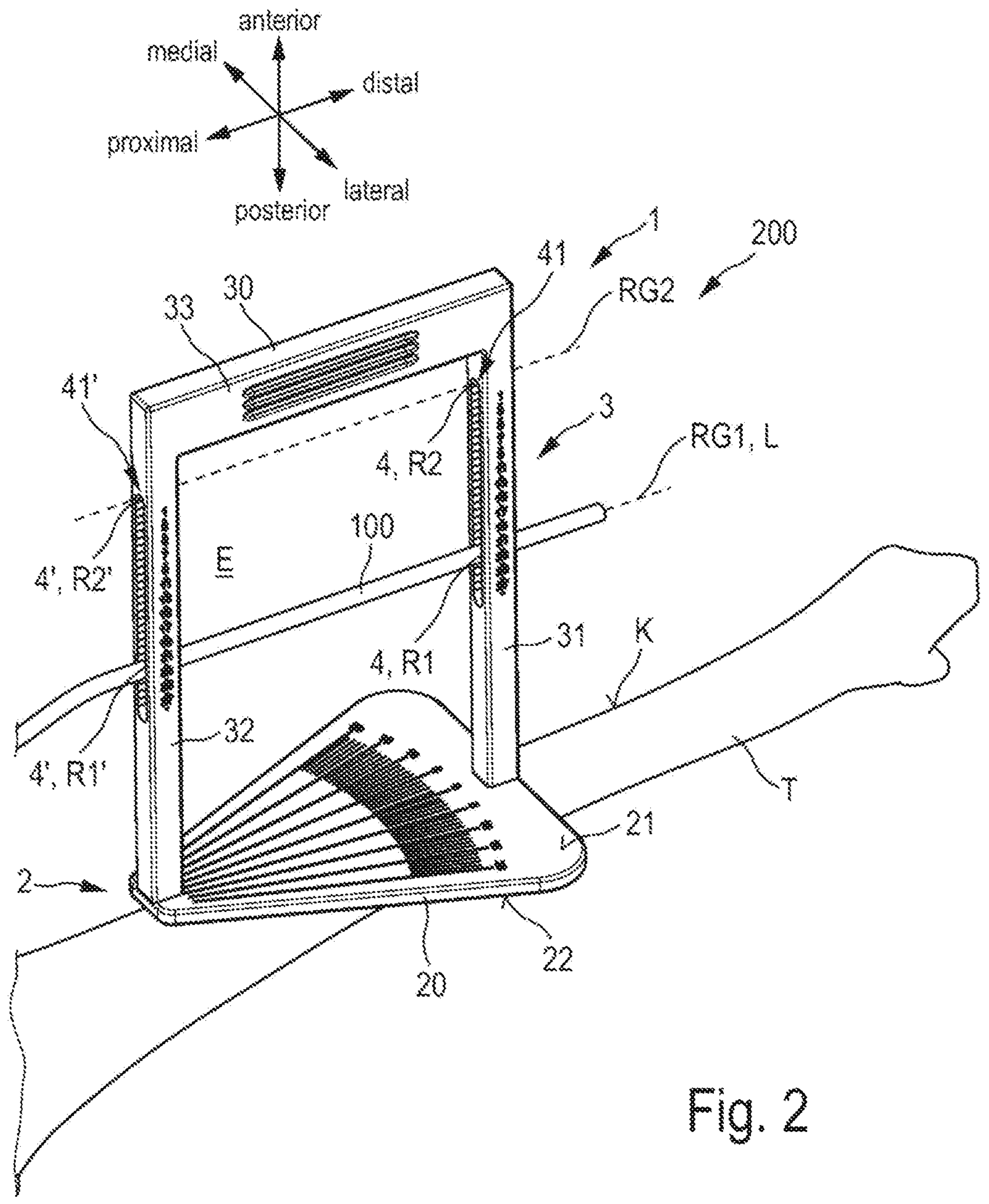
FIG. 2 shows a schematic perspective view of an exemplary intraoperative situation, in which the surgical device is being used in order to align an extramedullary alignment rod on a tibial front edge.
Figure 3:
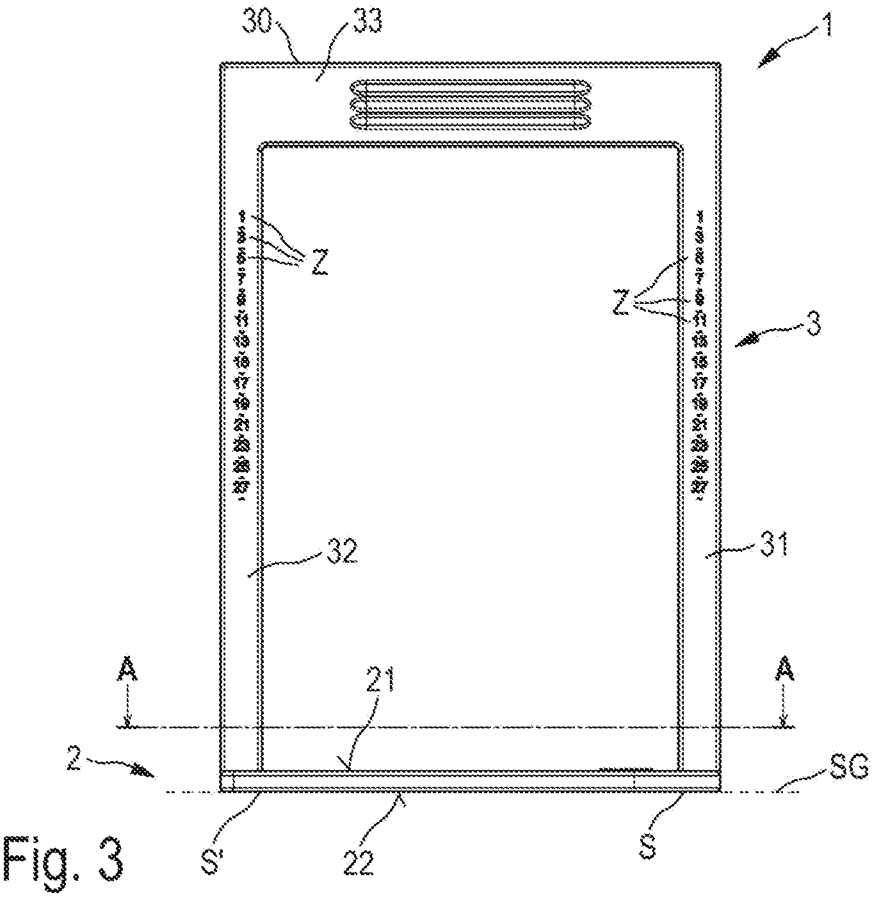
FIG. 3 shows the surgical device according to FIGS. 1 and 2 in a schematic side view with a medial viewing direction.
Figure 4:
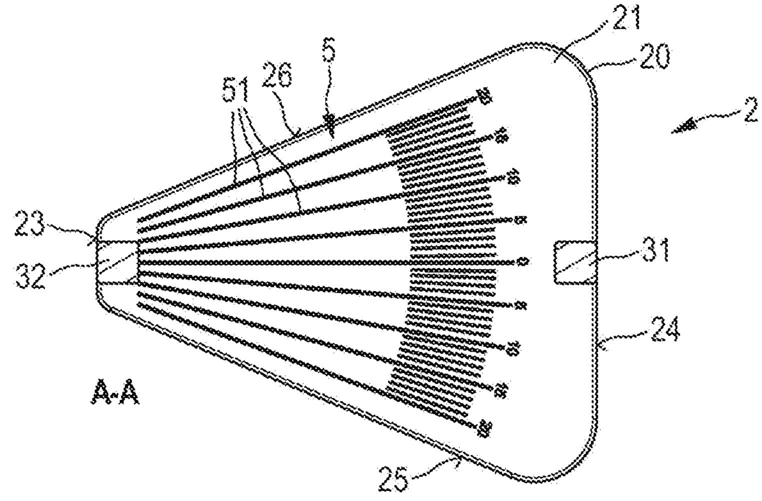
FIG. 4 shows the surgical device according to FIGS. 1 to 3 in a sectional view along a section line A-A according to FIG. 3.
Figure 5:
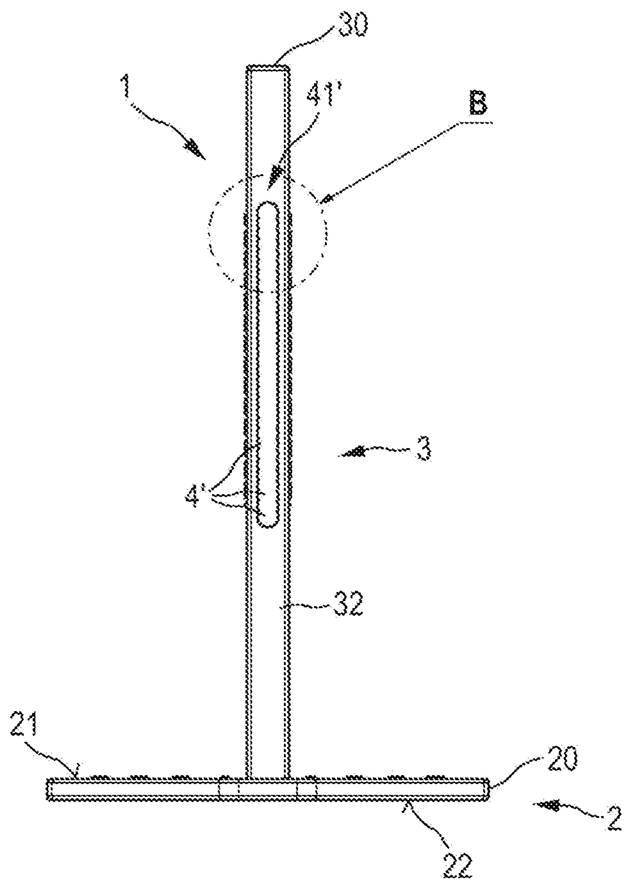
FIG. 5 shows the surgical device according to FIGS. 1 to 4 in a schematic rear view with a distal viewing direction.

According to FIGS. 1 to 6, a surgical device 1 for use in a total knee arthroplasty is provided. The surgical device 1 is used for aligning an extramedullary alignment rod 100. The surgical device 1 and the extramedullary alignment rod 100 form an arrangement 200 (FIG. 2).

The surgical device 1 has a supporting portion 2 and a reference portion 3.

In the embodiment according to FIGS. 1 to 6, the supporting portion 2 is configured as a plate 20.

The plate 20 has an upper side 21 oriented in an anterior direction and a lower side 22 oriented in a posterior direction. The lower side 22 is plane and is adapted to bear on an anterior edge K of a tibia T (see FIG. 2). The lower side 22 extends in mediolateral and proximodistal directions. Ends and/or points of the lower side 22 that lie opposite one another in a proximodistal direction in this case form two (imaginary) supporting geometries S, S'. These two supporting geometries S, S' are separated from one another along an (imaginary) supporting line SG. The supporting line SG extends in a proximodistal direction. The supporting geometry S may also be referred to as a distal supporting geometry S. The supporting geometry S' may also be referred to as a proximal supporting geometry S'.

The reference portion 3 projects in an anterior direction from the supporting portion 2. Regarding the present embodiment, the reference portion 3 projects in an anterior direction from the upper side 21 of the plate 20. The reference portion 3 has at least two reference geometries R1, R1'. The said reference geometries R1, R1' are separated from one another along an (imaginary) reference line RG1 that extends in a proximodistal direction. The reference geometry R1 may also be referred to as a distal reference geometry R1. The reference geometry R1' may also be referred to as a proximal reference geometry R1'.

The reference line RG1 is separated by an anterior distance A1 from the supporting line SG and extends parallel thereto. During use of the surgical device 1, the reference line RG1 is used as a reference for the alignment of the extramedullary alignment rod 100 (see FIG. 2). The extramedullary alignment rod 100 can be aligned by means of a parallel and/or coaxial alignment along the reference line RG1 indirectly parallel to the anterior edge K of the tibia T. The two reference geometries R1, R1' are each adapted for form-fit mounting of the extramedullary alignment rod 100. The form-fit mounting counteracts an undesired relative movement between the extramedullary alignment rod 100 and the surgical device 1.

In the embodiment shown, the reference portion 3 has two further reference geometries R2, R2'. In this context, the terms two first reference geometries R1, R1' and two second reference geometries R2, R2' may be used. The two second reference geometries R2, R2' are separated from one another in a proximodistal direction along a further reference line RG2. The reference line RG1 and the further reference line RG2 will also be referred to below as a first reference line RG1 and a second reference line RG2. The second reference line RG2 is aligned parallel to the first reference line RG1—and therefore also parallel to the supporting line SG. The second reference line RG2 is separated by an anterior second distance A2 from the supporting line SG. The second distance A2 is in the present case greater than the (first) distance A1 of the first reference line RG1. In the embodiment shown, the first reference line RG1 and the second reference line RG2 are arranged in a common sagittal plane E. The supporting line SG also lies in the sagittal plane E.

In the embodiment shown, the reference geometries R1, R1', R2, R2' are each configured as a bore 4, 4'. The bores 4, 4' may also be referred to as distal bores 4 and proximal bores 4'. Regarding the respective assignment to the first reference line RG1 or to the second reference line RG2, the terms first bores B1 and second bores B2 may also be used. All the bores are in the present case identically configured and/or elongated in a proximodistal direction. The first bores B1 are each elongated coaxially with the first reference line RG1. The second bores B2 are each elongated coaxially with the second reference line RG2.

In the embodiment shown, there are not merely two first and two second bores, but instead a multiplicity of bores arranged pairwise in a proximodistal direction. The multiplicity of bores form a distal row of bores 41 and a proximal row of bores 41'. In the embodiment shown, there are 27 proximal and distal bores and therefore 27 bore pairs. Each bore pair is assigned a reference line and correspondingly also an anterior distance from the supporting line SG.

Figure 6:
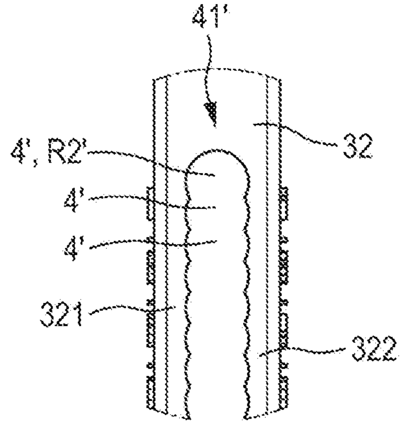
FIG. 6 shows an enlarged detail view of a region B according to FIG. 5.

The proximal bores 4' are arranged successively in an anteroposterior direction, immediately neighbouring bores each being connected to one another (see also FIG. 6). Same applies accordingly for the distal bores 4 of the distal row of bores 41. The extramedullary alignment rod 100 is held on its outer circumference with a form fit in the two rows of bores 41, 41'. Because of said connection between the bores 4, 4', the extramedullary alignment rod 100 can be displaced in an anteroposterior direction between the individual bore pairs of the rows of bores 41, 41'.

In the situation shown in FIG. 2, the extramedullary alignment rod 100 is mounted with a form fit in a first position. In this first position, the extramedullary alignment rod 100 is aligned coaxially with the first reference line RG1 and is held with a form fit at the first bores B1, which are assigned to the said reference line RG1, of the rows of bores 41, 41'. The form fit in this case acts in a mediolateral direction. In the proximodistal direction, the extramedullary alignment rod 100 is held in the rows of bores 41, 41' in such a way that it can move by gliding. Starting from the first position shown, the extramedullary alignment rod 100 can be displaced in the longitudinal direction of the rows of bores 41, 41' in an anterior direction towards the second reference line RG2. In this case, the outer circumference of the extramedullary alignment rod 100 switches between the individual bores 4, 4' of the two rows of bores 41, 41'.

In the embodiment shown, the reference portion 2 is resiliently flexible in the region of the bores 4, 4' and/or rows of bores 41, 41'. The flexible properties are in the present case achieved in a manner which will be described in more detail. The resilient flexibility makes it possible for the extramedullary alignment rod 100 to be "switched" in the manner described above from one bore pair into a neighbouring bore pair.

In the embodiment shown, the reference portion is configured as a frame 30.

The frame 30 in the present case has two longitudinal branches 31, 32 and one transverse branch 33.

The longitudinal branches 31, 32 may also be referred to as a distal longitudinal branch 31 and a proximal longitudinal branch 32. The two longitudinal branches 31, 32 are each elongated in an anteroposterior direction. In the present case, the two longitudinal branches 31, 32 are aligned parallel to one another. The longitudinal branches 31, 32 are separated from one another in a proximodistal direction. The longitudinal branches 31, 32 project in an anterior direction from the supporting portion 2. In particular, the longitudinal branches 31, 32 in the present case project from the upper side 21 of the plate 20. In the present case, the longitudinal branches 31, 32 are aligned orthogonally to the upper side 21. The longitudinal branches 31, 32 in the present case each have a rectangular, in particular square, cross-sectional shape (see FIG. 4). For improved display and easy identification of the respective position of the extramedullary alignment rod 100, the longitudinal branches 31, 32 in the present case are each provided with marking numbers Z. In the embodiment shown, the marking numbers Z are numbered sequentially from 1 to 27.

The transverse branch 33 is elongated in a proximodistal direction between the two longitudinal branches 31, 32. The transverse branch 33 is arranged at one end of the two longitudinal branches 31, 32. The supporting portion 2, in particular the plate 20, is in the present case arranged at the other end of the longitudinal branches 31, 32. The transverse branch 33 is oriented parallel to the upper side 21 and/or orthogonally to the two longitudinal branches 31, 32.

In the present case, the proximal bores 4' and/or the proximal row of bores 41' are introduced into the proximal longitudinal branch 32. The distal bores 4 and/or the distal row of bores 41 are introduced into the distal longitudinal branch 31.

The bores 4, 4' extend through the cross section of the respective longitudinal branch 31, 32. The longitudinal branches 31, 32 are thin-walled in a mediolateral direction in the region of the rows of bores 41, 41' (see FIGS. 5, 6). The bores 4' of the row of bores 41 are in the present case delimited in a mediolateral direction by a medial cheek 321 and a lateral cheek 322 of the proximal longitudinal branch 32 (see FIG. 6). The said cheeks 321, 322 are thin-walled and are consequently resiliently flexible in comparison with the other regions of the longitudinal branch 32. The resilient flexibility allows latching and movement of the extramedullary alignment rod 100 according to requirements. The disclosure relating to the proximal longitudinal branch 32 also applies, mutatis mutandis, for the distal longitudinal branch 31.

In the embodiment according to FIGS. 1 to 6, the upper side 21 of the plate 20 has a scale 5. The scale 5 has graduations 51. The graduations 51 fan out in a distal direction and each represent a value of a *varus/valgus* angle of the tibia T. The *varus/valgus* angle of the tibia T can be read on the scale 5. In the present case, an alignment of the anterior edge K in the sagittal plane E corresponds to a *varus/valgus* angle of 0° (see FIG. 4).

The plate 20 is in the present case adapted in its shaping to its function as a display surface for the scale 5. In particular, the plate 20 has a proximal edge 23, an opposite distal edge 24, a lateral edge 25 and an opposite medial edge 26. The proximal edge 23 and the distal edge 24 are parallel to one another. The proximal edge 23 is shorter than the distal edge 24. The lateral edge 25 is inclined laterally outwards in a distal direction starting from the proximal edge 23. The medial edge is medially inclined outwards symmetrically with respect thereto. The lateral edge 25 and the medial edge 26 are accordingly not parallel to one another.

In one embodiment, which is not shown in the figures, the reference portion is configured not for instance as a frame but instead as a kind of plate. The reference geometries are in this embodiment configured not for instance as a bore but instead as a latching recess that is open in a medial or lateral direction. The present configuration of the reference portion 3 as a frame 30 is advantageous but not essential for the present disclosure.

Figure 7:
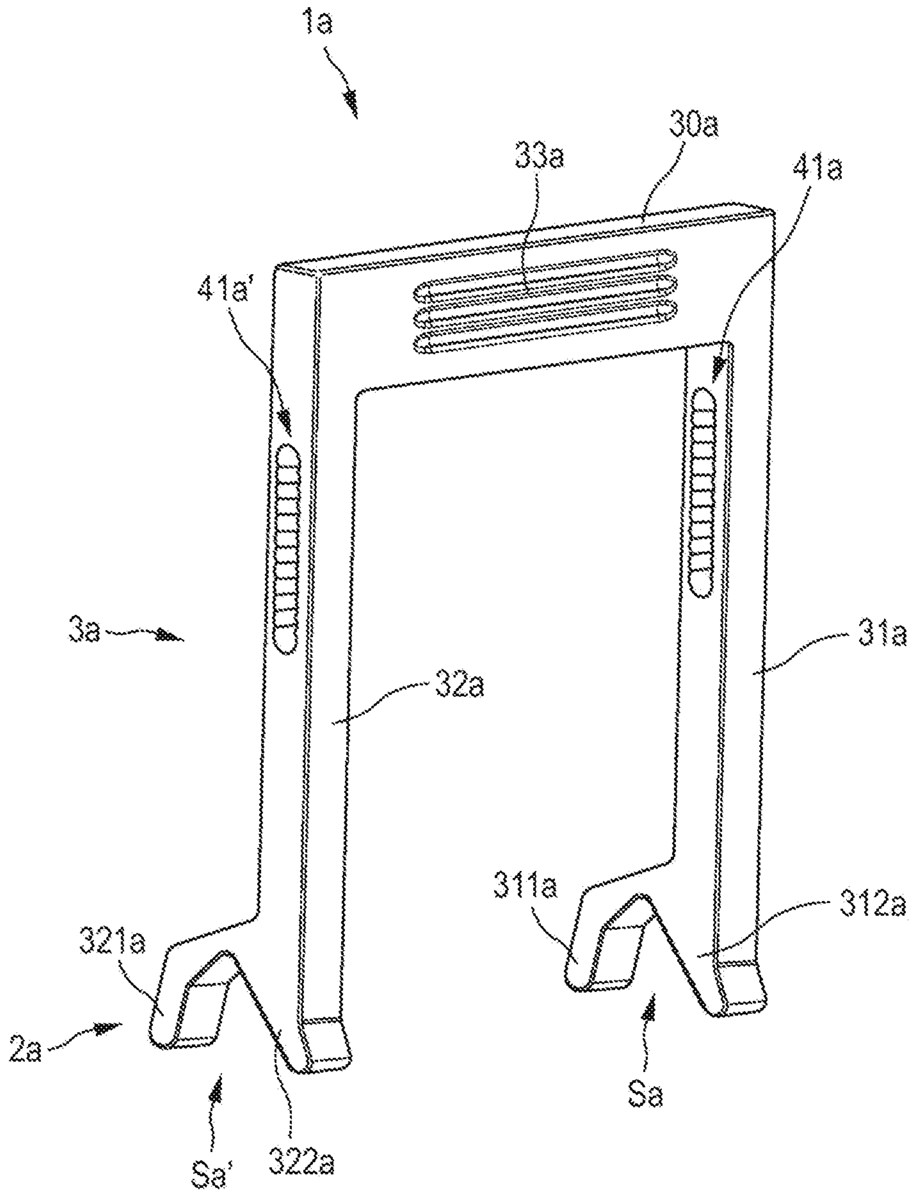
FIG. 7 shows a schematic perspective view of another embodiment of a surgical device according to the present disclosure.
Figure 8:
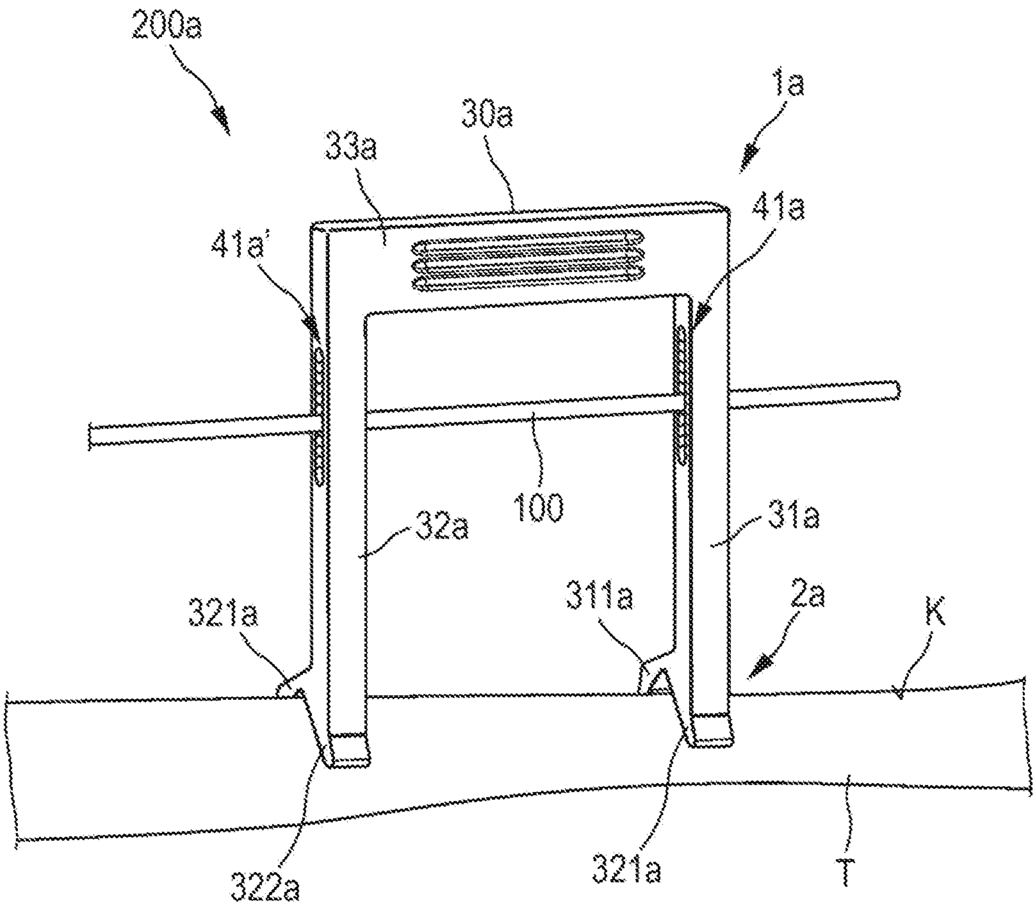
FIG. 8 shows a schematic perspective view of an exemplary intraoperative situation, in which the surgical device according to FIG. 7 is being used to align an extramedullary alignment rod on a tibial front edge.

FIGS. 7 and 8 show another embodiment of a surgical device 1*a* according to the present disclosure. The surgical device 1*a* is substantially identical to the surgical device 1 according to FIGS. 1 to 6. To avoid repetition, only major differences will be described below. Component parts and/or portions of the surgical device 1*a* according to FIGS. 7 and 8 that are also present with an identical configuration and/or function in the surgical device 1 according to FIGS. 1 to 6 will not be explained separately. Instead, mention of and explicit reference to the surgical device 1 is made.

The surgical device 1*a* has a differently configured supporting portion 2*a*. The latter is formed not as a plate but instead by end portions of the longitudinal branches 31*a*, 32*a*. In this case, a posterior end of the distal longitudinal branch 31*a* forms the distal supporting geometry Sa. The corresponding end portion of the proximal longitudinal branch 32*a* forms the proximal supporting geometry Sa'.

In the embodiment shown, the end portions and/or supporting geometries Sa, Sa' each have a fork shape with a first prong portion 311*a*, 321*a* and a second prong portion 312*a*, 322*a*. Expressed in other words, the longitudinal branches 31*a*, 32*a* are each bifurcated at one end into the said prongs 311*a*, 312*a* and 321*a*, 322*a*, respectively. The bifurcated and/or fork-shaped configuration counteracts slipping of the surgical device 1*a* from the anterior edge K (see FIG. 8). The surgical device 1*a* forms a further arrangement 200*a* together with extramedullary alignment rod 100.

Further structural and/or functional features are shown in FIGS. 9 to 13. The features shown there may each be combined individually or in combination with the features of the surgical devices 1, la and/or arrangements 200, 200*a*.

Figure 9:
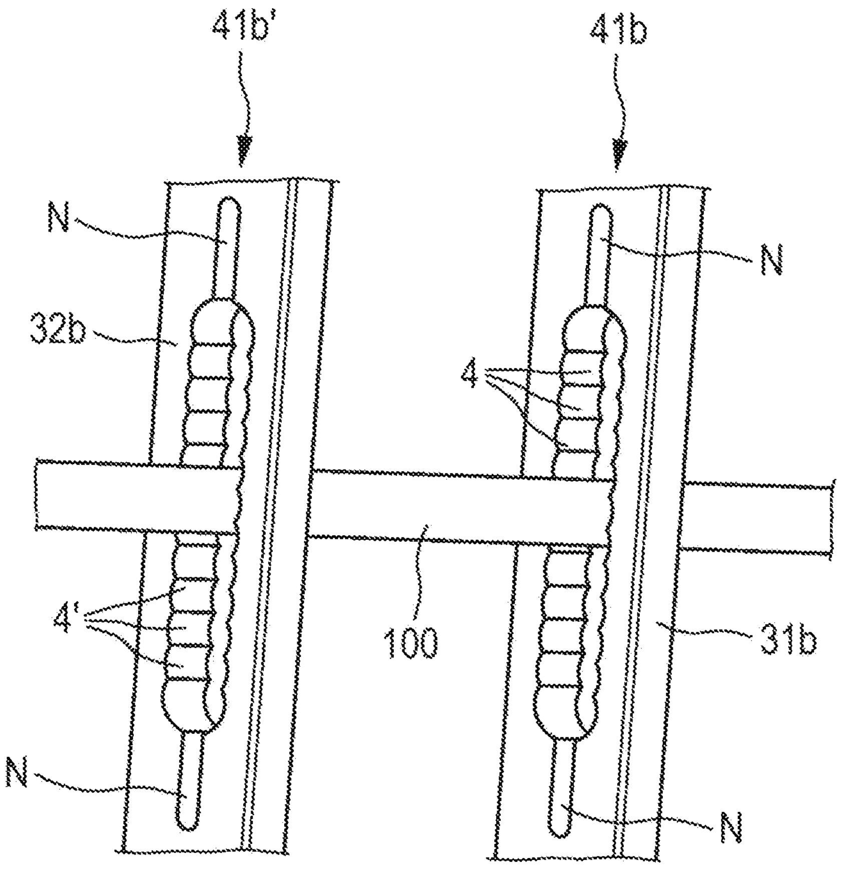
FIG. 9 shows a partially cutaway perspective detail view illustrating further features.

FIG. 9 shows rows of bores 41*b*, 41*b*'. The rows of bores 41*b*, 41*b*' are substantially identical to the rows of bores 41*a*, 41*a*' of the surgical device 1*a* and the rows of bores 41, 41' of the surgical device 1. The rows of bores 41*b*, 41*b*' each have a longitudinal slot N at their opposite extreme ends. The longitudinal slots N enhance the already explained resilient flexibility of the longitudinal branches 31*b*, 32*b*. The longitudinal slots N are particularly advantageous when the surgical device is manufactured with thick walls and/or from metal in the region of the rows of bores.

Figure 10:
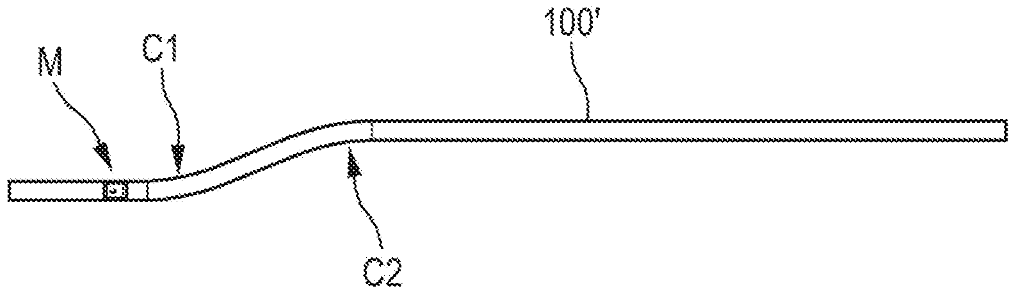
FIG. 10 shows a schematic side view of an embodiment of an extramedullary alignment rod.
Figure 11:
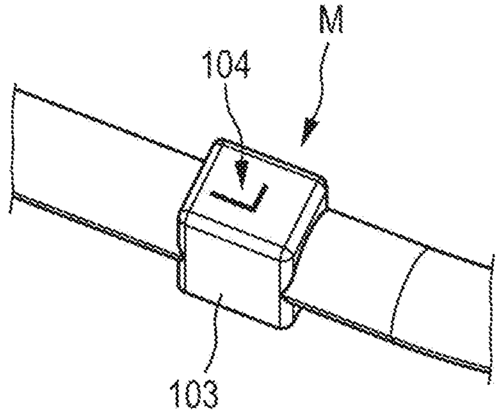
FIG. 11 shows a schematic perspective view of a detail region of the extramedullary alignment rod according to FIG. 10.

FIGS. 10 and 11 show a differently configured extramedullary alignment rod 100'. The extramedullary alignment rod 100' may be used instead of the extramedullary alignment rod 100 respectively with one of the surgical devices 1, la. The alignment rod 100' has a first curve C1 and a second curve C2 (see FIG. 10). The two curves C1, C2 subdivide the alignment rod 100' into two parallel-offset elongated portions (without reference sign). The alignment rod 100' furthermore has a marking M in the form of a cuboid element 103. The cuboid element 103 is provided with a symbol 104. The symbol 104 is in the present case the letter "L".

In the embodiment shown, the cuboid element 103 is provided on its side facing away from the symbol 104 with a further symbol (without reference sign) which cannot be seen in the figures. The further symbol is in the present case the letter "R".

The extramedullary alignment rod 100' can be inserted in such a way that the symbol 104 ("L") is aligned in an anterior direction. In this case, the extramedullary alignment rod 100' is adapted for use on the left leg. The extramedullary alignment rod 100' can furthermore be inserted after being rotated through 180° about its longitudinal axis, so that the further symbol ("R") is aligned in an anterior direction—and the symbol 104 in a posterior direction. In this case, the extramedullary alignment rod 100' is adapted for use on the right leg.

The marking M therefore indicates to the surgeon the leg on which to use the extramedullary alignment rod 100'.

Figure 12:
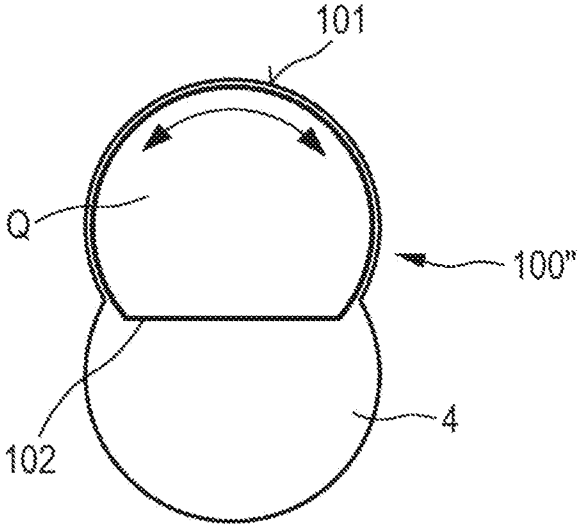
FIGS. 12 and 13 show detail views for illustrating further features of the extramedullary alignment rod and/or of the surgical devices.
Figure 13:
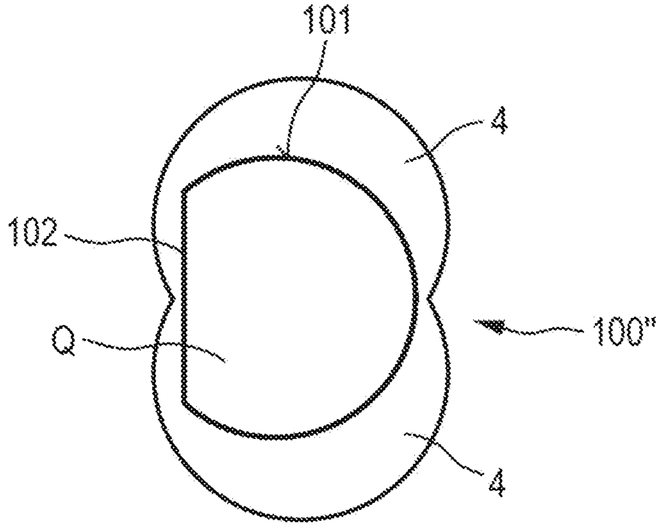

FIGS. 12 and 13 show features of a further alignment rod 100". The alignment rod 100" is shown in a proximal viewing direction onto its cross-section Q. The cross-section Q is not rotationally symmetrical. In contrast thereto, the cross sections (without references) of the extramedullary alignment rods 100, 100' are rotationally symmetrical, in particular circular. The outer circumference 101 of the alignment rod 100" has a radial flat 102. In the situation shown with the aid of FIG. 12, the alignment rod 100" is held with a form fit in a mediolateral and anteroposterior direction in an upper of the two bores 4. In the embodiment shown, the bores 4 are not, or at least not sufficiently, resiliently flexible in a radial direction to allow a latching relocation of the alignment rod 100". For moving the alignment rod 100" from the upper into the lower of the two bores 4, the alignment rod 100" is rotated about its longitudinal axis. Starting from the position shown in FIG. 12, a rotation through 90° is carried out in the clockwise direction. Alternatively, a rotation may be carried out through 90° anticlockwise. By the modified position of the radial flat 102, an effective diameter of the alignment rod 100" is changed. The alignment rod 100" can readily be relocated from the upper into the lower of the two bores 4 in the position rotated in this way. For form-fit mounting at the lower of the two bores 4, the alignment rod 100" is again rotated about its longitudinal axis so that the radial flat 102 faces either in an anterior direction or in a posterior direction.

The invention claimed is:

1. A surgical device for aligning an extramedullary alignment rod during a total knee arthroplasty, the surgical device comprising:

a supporting portion having at least two supporting geometries separated from one another along a supporting line that extends in a proximodistal direction and are each adapted for support on an anterior edge of a tibia; and a reference portion that projects in an anterior direction from the supporting portion and has at least two reference geometries separated from one another along a reference line that extends in the proximodistal direction, the reference line being separated from the supporting line by an anterior distance and extending parallel to the supporting line, the at least two reference geometries and/or the reference line serving as a reference for aligning the extramedullary alignment rod, the at least two reference geometries each adapted for at least mediolaterally form-fit mounting against an outer surface of the extramedullary alignment rod;

wherein the reference portion is configured as a frame having two longitudinal branches and a transverse branch, the two longitudinal branches being separated from one another in the proximodistal direction and each being elongated in an anteroposterior direction and having a respective one or more of the at least two reference geometries, and the transverse branch being elongated in the proximodistal direction between the two longitudinal branches and connecting the two longitudinal branches to one another.

2. The surgical device according to claim 1, wherein the reference portion has at least two first reference geometries separated from one another along a first reference line, and two second reference geometries separated from one another along a second reference line, the first reference line being separated by an anterior first distance from the supporting line and the second reference line being separated by an anterior second distance from the supporting line.

3. The surgical device according to claim 2, wherein the at least two first reference geometries and the two second reference geometries are each configured as a bore, so that there are at least two first bores and at least two second bores.

4. The surgical device according to claim 3, wherein the at least two first bores and the at least two second bores are connected to one another in an anteroposterior direction, so that the extramedullary alignment rod is displaceable starting from a mounting position on the at least two first bores in the anteroposterior direction and/or in a radial direction into a mounting position on the at least two second bores, and vice versa.

5. The surgical device according to claim 3, wherein the reference portion is resiliently flexible in a region of the at least two first bores and the at least two second bores.

6. The surgical device according to claim 1, wherein the two longitudinal branches each have a row of bores with a plurality of bores following one another in an anteroposterior direction as reference geometries.

7. The surgical device according to claim 1, wherein the supporting portion is formed by end portions of the two longitudinal branches, each end portion respectively having one of the at least two supporting geometries.

8. The surgical device according to claim 1, wherein the supporting portion is configured as a plate having a lower side oriented in a posterior direction and an upper side oriented in an anterior direction, the lower side being planar and having and/or forming the at least two supporting geometries, and the reference portion projecting from the upper side.

9. The surgical device according to claim 8, wherein the plate has a scale arranged on the upper side with graduations fanning out in a distal direction, the graduations each representing a value of a *varus/valgus* angle of the tibia.

10. A surgical system comprising:

the surgical device according to claim 1; and an extramedullary alignment rod.

11. The surgical device according to claim 1, wherein the transverse branch is rigidly connected to the two longitudinal branches.

12. A surgical device for aligning an extramedullary alignment rod during a total knee arthroplasty, the surgical device comprising:

a supporting portion having at least two supporting geometries separated from one another along a supporting line that extends in a proximodistal direction and are each adapted for support on an anterior edge of a tibia; and a reference portion that projects in an anterior direction from the supporting portion and has at least two reference geometries separated from one another along a reference line that extends in the proximodistal direction, the reference line being separated from the supporting line by an anterior distance and extending parallel to the supporting line, the at least two reference geometries and/or the reference line serving as a reference for aligning the extramedullary alignment rod, the at least two reference geometries each adapted for at least mediolaterally form-fit mounting of the extramedullary alignment rod;

wherein:

the reference portion has at least two first reference geometries separated from one another along a first reference line, and two second reference geometries separated from one another along a second reference line, the first reference line being separated by an anterior first distance from the supporting line and the second reference line being separated by an anterior second distance from the supporting line, and the at least two first reference geometries and the two second reference geometries are each configured as a bore, so that there are at least two first bores and at least two second bores.

13. A surgical device for aligning an extramedullary alignment rod during a total knee arthroplasty, the surgical device comprising:

a supporting portion having at least two supporting geometries separated from one another along a supporting line that extends in a proximodistal direction and are each adapted for support on an anterior edge of a tibia; and a reference portion that projects in an anterior direction from the supporting portion and has at least two reference geometries separated from one another along a reference line that extends in the proximodistal direction, the reference line being separated from the supporting line by an anterior distance and extending parallel to the supporting line, the at least two reference geometries and/or the reference line serving as a reference for aligning the extramedullary alignment rod, the at least two reference geometries each adapted for at least mediolaterally form-fit mounting of the extramedullary alignment rod;

wherein:

the reference portion is configured as a frame having two longitudinal branches and a transverse branch, the two longitudinal branches being separated from one another in the proximodistal direction and each being elongated in an anteroposterior direction and having a respective one or more of the at least two reference geometries, and the transverse branch being elongated in the proximodistal direction between the two longitudinal branches and connecting the two longitudinal branches to one another, the supporting portion is formed by end portions of the two longitudinal branches, each end portion respectively having one of the at least two supporting geometries, and the at least two supporting geometries each have a fork shape with a first prong portion and a second prong portion.

14. A surgical device for aligning an extramedullary alignment rod during a total knee arthroplasty, the surgical device comprising:

a supporting portion having at least two supporting geometries separated from one another along a supporting line that extends in a proximodistal direction and are each adapted for support on an anterior edge of a tibia; and a reference portion that projects in an anterior direction from the supporting portion and has at least two reference geometries separated from one another along a reference line that extends in the proximodistal direction, the reference line being separated from the supporting line by an anterior distance and extending parallel to the supporting line, the at least two reference geometries and/or the reference line serving as a reference for aligning the extramedullary alignment rod, the at least two reference geometries each adapted for at least mediolaterally form-fit mounting of the extramedullary alignment rod;

wherein the supporting portion is configured as a plate having a lower side oriented in a posterior direction and an upper side oriented in an anterior direction, the lower side being planar and having and/or forming the at least two supporting geometries, and the reference portion projecting from the upper side.

* * * * *